United States Patent [19]
Dabi et al.

[11] Patent Number: 5,470,326
[45] Date of Patent: Nov. 28, 1995

[54] CLEAN DRY FACING NEEDLED COMPOSITE

[75] Inventors: Shmuel Dabi, Highland Park; Kays Chinai, Burlington, both of N.J.

[73] Assignee: McNeil-PPC, Inc., Milltown, N.J.

[21] Appl. No.: 226,438

[22] Filed: Apr. 12, 1994

Related U.S. Application Data

[63] Continuation of Ser. No. 736,675, Jul. 26, 1991, abandoned.

[51] Int. Cl.[6] .............................. A61F 13/15; A61F 13/20
[52] U.S. Cl. ..................... 604/383; 604/358; 604/367; 604/378; 604/381; 604/384; 604/385.1
[58] Field of Search .................... 604/358, 362, 604/366, 367, 369, 370, 378, 381, 383–384, 385.1; 602/45, 47, 52, 58–59; 428/131, 137, 138, 286, 287, 913

[56] References Cited

U.S. PATENT DOCUMENTS

| | | | |
|---|---|---|---|
| 810,130 | 1/1906 | Green . | |
| 2,418,907 | 4/1947 | Schreiber . | |
| 2,551,663 | 5/1951 | Fox | 128/290 |
| 3,122,140 | 2/1964 | Crowe, Jr. | 604/369 |
| 3,122,142 | 2/1964 | Crowe, Jr. | 604/369 |
| 3,545,442 | 12/1970 | Wicker et al. | 604/383 |
| 3,811,445 | 5/1974 | Dostal . | |
| 3,817,827 | 6/1974 | Benz | 162/113 |
| 3,871,378 | 3/1975 | Duncan et al. | 604/372 |
| 3,889,679 | 6/1975 | Taylor | 128/287 |
| 3,927,673 | 12/1975 | Taylor . | |
| 3,994,299 | 11/1976 | Karami | 604/378 |
| 4,077,410 | 3/1978 | Butterworth et al. | 604/378 |
| 4,377,615 | 3/1983 | Suzuki et al. | 428/286 |
| 4,605,402 | 8/1986 | Iskra | 604/368 |
| 4,634,440 | 1/1987 | Widlund et al. | 604/383 |
| 4,643,727 | 2/1987 | Rosenbaum | 604/369 |
| 4,676,784 | 6/1987 | Erdman et al. | 604/368 |
| 4,676,786 | 6/1987 | Nishino | 604/378 |
| 4,726,976 | 2/1988 | Karami et al. | 604/366 |
| 5,078,710 | 1/1992 | Suda et al. | 604/383 |

FOREIGN PATENT DOCUMENTS 151018  8/1985  European Pat. Off. .

OTHER PUBLICATIONS

Japanese Fiber Association, "A Survey of Fiber", 1969 [translation included].

*Primary Examiner*—Randall L. Green
*Assistant Examiner*—P. Zuttarelli

[57] ABSTRACT

Novel facing materials and methods for their manufacture are provided by this invention. The facing material includes at least a fibrous top layer for engaging body fluid and a generally opaque middle layer. A portion of the facing material is disposed, preferably by piercing, through the generally opaque middle layer to establish a fluid path through the generally opaque middle layer. In the preferred embodiment, the facing material includes a bottom layer having a capillary structure for drawing the body fluid from the fibrous top layer. In this preferred embodiment, the fibrous top layer extends through the generally opaque middle layer to provide fluid communication between the fibrous top layer and the bottom layer. These composite structures provide a clean/dry facing material that has a comfort of a textile facing and the high opacity of apertured thermoplastic films.

23 Claims, 2 Drawing Sheets

SEE FIG. 3

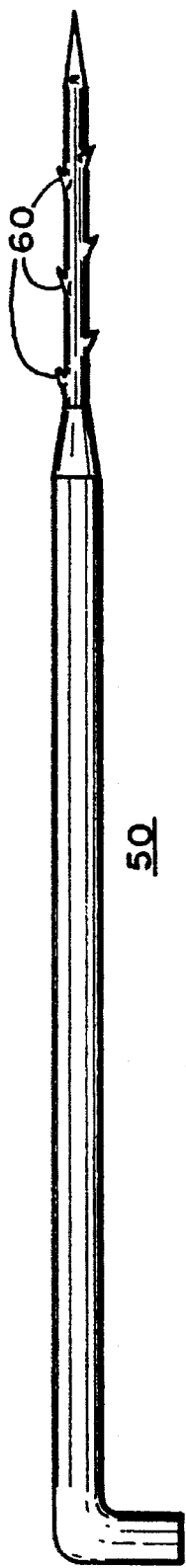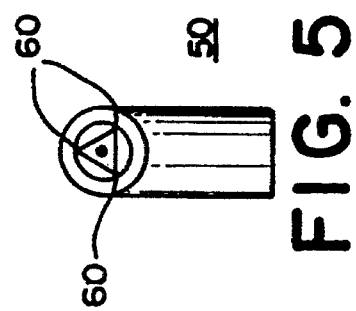

CLEAN DRY FACING NEEDLED COMPOSITE

This is a continuation of application Ser. No. 07/736,675, filed Jul. 26, 1991, now abandoned.

FIELD OF THE INVENTION

This invention relates to clean and dry facing materials suitable for use as body-facing layers in diapers and sanitary napkins, and more particularly, to methods for providing better "hiding power" and comfort to consumers of such products.

BACKGROUND OF THE INVENTION

Absorbent products, such as diapers and sanitary napkins, generally utilize three distinctive layers: a top, body-facing layer, normally a fluid permeable sheet for engaging with body fluids, a core, usually a fluid absorbent material such as wood pulp for retaining fluids, and a bottom layer, usually a fluid impervious barrier film. In these constructions, body fluids permeate through the body-facing layer into the absorbent core where they are absorbed and stored. Traditionally, the body-facing layer has been made from a soft, non-woven web which generally allows fluid to migrate into the absorbent core and separates the body from the discharge to keep the skin clean and dry. The main drawback to such non-woven facing materials is that some fluid is often retained in the capillary structure of the web, resulting in a wet surface disposed against the user. Recently, facing materials made from apertured film, such as polyethylene, have been used to overcome the wetness problem. In the absence of capillaries, very little fluid is retained on the film and a drier surface against the skin is obtained. Apertured films have the added advantage that, since they are more opaque than non-woven webs, they can better hide the stained absorbent core. However the plastic apertured films generally are less comfortable to wear than non-woven facing materials.

Some of the problems associated with comfort and performance of absorbent products have been addressed in such patents as: Fox, U.S. Pat. No. 2,551,663, issued May 8, 1951; Erdman et al., U.S. Pat. No. 4,676,784, issued Jun. 30, 1987; Nishino, U.S. Pat. No. 4,676,786, issued Jun. 30, 1987; Rosenbaum, U.S. Pat. No. 4,643,727, issued Feb. 17, 1987; Taylor, U.S. Pat. No. 3,889,679, issued Jun. 17, 1975; and Green, U.S. Pat. No. 810,130, issued Jan. 16, 1906.

Erdman et al., for example, describes absorbent products comprising resilient fibers and super absorbent materials. This reference teaches the use of a hydrophilic porous cover and a fibrous superstructure containing at least about 10% by weight superabsorbent. The fibrous superstructure comprises apertures or strips of a web in a configuration which provides channels for attracting fluid.

Nishino describes a paper diaper having a surface layer of fluff pulp with a "partition layer" having spaced openings therein, followed by a "crust layer" disposed under the partition layer to receive and diffuse fluids in an oriented manner.

Rosenbaum describes an absorbent pad having an intermediate "plastic bubble layer" covered on either side with a continuous layer of absorbent material. The bubble layer of this reference serves as a reservoir for fluid that is eventually syphoned around the edges of the bubble layer for storage.

Taylor discloses a disposable diaper comprising an absorbent body and a water impervious backing sheet. The absorbent body is provided with a plurality of fluid passages for distributing fluid to more remote portions of its structure.

Green describes an absorbent bandage which utilizes internal cells for the quick reception of fluid. These cells distribute the fluid to an absorbent fibrous mass for storage. The bandage can further comprise a fabric cover.

Fox describes a catamenial diaper having an elongated pad having a longitudinally extending chamber therein and a plurality of vertical openings for transmitting fluid from the top of the pad to the chamber. This catamenial diaper employs rubber materials and is designed to be reusable.

Although these references disclose useful techniques for comfort and absorption, there has been a long-felt need for a composite cover which combines the comfort of a fibrous web with the opacity and dryness of an apertured film, while overcoming their deficiencies.

SUMMARY OF THE INVENTION

Unique facing materials suitable for use in absorbent products and methods for manufacturing these facing materials are provided by this invention. The facing materials include a generally opaque apertured middle layer sandwiched between a fibrous top layer for engaging body fluids and a bottom layer having a capillary structure for drawing body fluids from the fibrous top layer. In an important aspect of this invention, the fibrous top layer extends through the apertures of the generally opaque middle layer and communicates with the bottom layer for providing fluid transfer from the fibrous top layer into the bottom layer.

This invention is also intended to cover a facing material having only a fibrous top layer and a generally opaque apertured layer. In such an embodiment, a portion of the fibrous top layer would be disposed through the apertures of the opaque layer, as described above. The resulting two-layered composite would be useful as a body-facing surface for absorbent elements containing wood pulp and the like, whereby fluid would be directed from the fibrous top layer, through the apertures of the opaque layer and into the absorbent element for storage.

This invention also includes a method of preparing a facing material which includes the steps of providing a tri-layered flexible composite including a fibrous top layer, a generally opaque middle layer and a bottom layer having a capillary structure for drawing body fluid. The method next includes the step of perforating the composite to provide a plurality of apertures through the generally opaque middle layer. The perforation step disposes a portion of the fibrous top layer through the apertures for providing fluid transfer from the fibrous top layer into the bottom layer.

The flow of body fluids within the facing materials of this invention can be further improved by increasing the density of the web of the bottom layer relative to the top layer. Additional improvements can be generated by treating the bottom layer with hydrophilic chemicals and/or treating the fibrous top layer with hydrophobic chemicals.

Accordingly, composite structures having a clean, dry facing surface are provided without sacrificing the comfort associated with a textile or non-woven web facing. The composites also possess high opacity and hide staining effectively for a pleasing aesthetic appearance.

It is, therefore, an object of this invention to provide facing materials suitable for use in diapers and sanitary napkins which provides for efficient removal of body fluids away from the skin of the user.

It is another object of this invention to provide facing materials having a generally opaque appearance for hiding absorbed body fluids while maintaining a comfortable, fibrous texture.

With these and other objects in view which will become apparent to one skilled in the art as the description proceeds, this invention resides in the novel construction, combination, arrangement of parts, and methods substantially as hereinafter described and more particularly defined by the attached claims.

BRIEF DESCRIPTION OF THE DRAWINGS

The accompanying drawings illustrate a preferred embodiment of the invention devised for the practical application of the principles thereof, and in which:

FIG. 4: is an enlarged side view of a preferred single blade piercing barbed needle;

FIG. 5: is an end view of the needle of FIG. 4; and

FIG. 6: is a side view of a preferred double blade piercing, barbed needle.

DETAILED DESCRIPTION OF THE INVENTION

Figure 1:
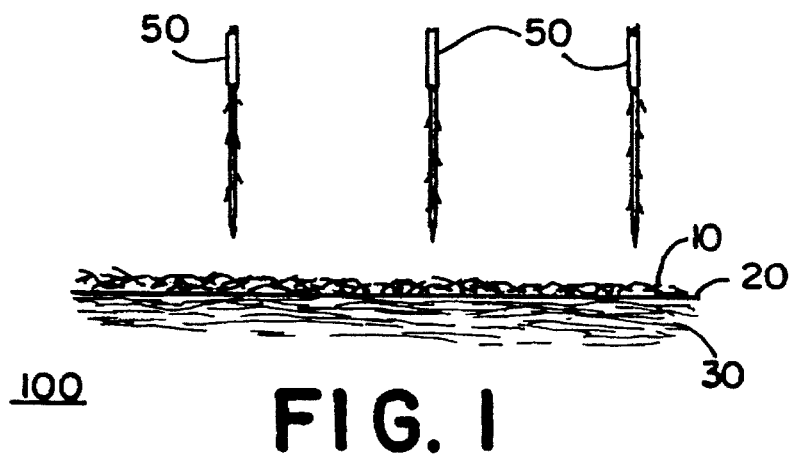
FIG. 1: is a cross-sectional, diagrammatic view of a preferred facing material of this invention illustrating the insertion of piercing barbed needles.

Preferred operative embodiments espousing the principal objects of this invention will now be described. In one embodiment of this invention, a facing material suitable for use in diapers and the like is provided which comprises a fibrous top layer for engaging a body fluid, a generally opaque apertured middle layer, and a bottom layer having a capillary structure for drawing body fluid from the fibrous top layer. The fibrous top layer extends through the generally opaque middle layer and communicates with the bottom layer for providing fluid transfer from the fibrous top layer into the bottom layer. As used herein, the term "generally opaque" refers to the ability of the material to impede the transmission of light. More preferably, the generally opaque middle layer of this invention is relatively impervious to light.

In another preferred embodiment of this invention, a facing material is provided having a fibrous top layer for engaging body fluid which comprises a plurality of hydrophobic fibers having a denier of about 3 or greater. Beneath the fibrous top layer of this embodiment, is a generally opaque polymeric middle layer having a thickness of from about 0.2 to 2 mils. Following the middle layer, is a bottom layer capable of generating a greater capillary pressure than the fibrous top layer. The generally opaque middle layer has apertures therethrough, whereby a portion of the fibers of the fibrous top layer are disposed through the apertures and into the bottom layer for providing fluid transfer from said fibrous top layer into said bottom layer.

Alternatively, the facing material can comprise two layers of material: a top fibrous layer disposed on a generally opaque apertured middle layer. In such an embodiment, barbed needles can be employed to pull through a portion of the fibrous top layer through the generally opaque middle layer. The resulting two-layered composite can be used as a body-facing surface for absorbing elements, such as those containing wood pulp. It will be understood by those of ordinary skill in the art that this embodiment could be favorably employed to achieve the overall benefits described for the three-layered composite described above.

Some of the dynamic principles believed to be responsible for the benefits achieved by these facing materials will now be described. It is well known that a capillary pressure acting on a given fluid is a function of the dimensions of the capillaries and their wettability as shown in the following equation:

$$/\Delta p = \frac{2\gamma \cos - \theta°}{r} \tag{1}$$

where $/\Delta$=capillary pressure $\gamma$=surface tension of fluid $\theta$=contact angle between the fluid and the capillary wall $r$=radius of the capillary The fibrous mass of the facing material of this invention can be regarded as a matrix containing interconnecting voids, which form a capillary structure. The capillaries can be made larger or smaller by decreasing or increasing the density of the web, if a web is chosen or by increasing or decreasing the fiber denier. Thus, in order to make a fibrous structure which allows the passage of fluid without retaining it, one would preferably make a low density web with large pores. An additional step to reduce the capillary pressure and minimize the fluid holding capability is to select fibers with a non-wettable surface. According to equation 1, low capillary pressure is obtained when the contact angle between the fluid and the solid is $\theta=90°$. Thus, water repellent surfaces, which form a large contact angle, are ideally suited for making the non-retentive web, e.g. the fibrous top layers of this invention.

Figure 2:
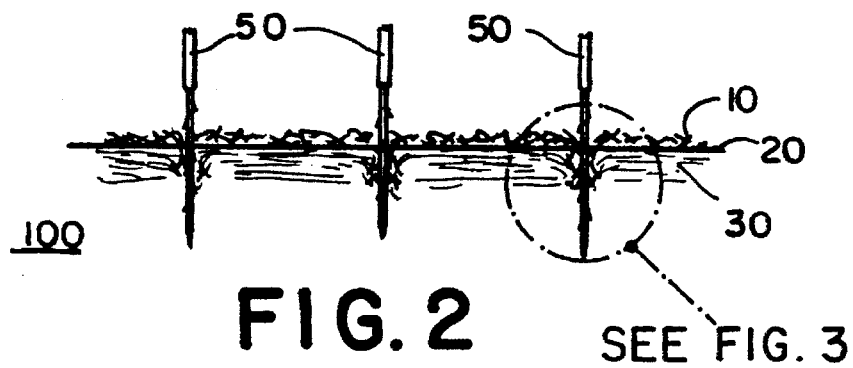
FIG. 2: is the preferred facing material of FIG. 1 after said needles are withdrawn from the material.
Figure 3:
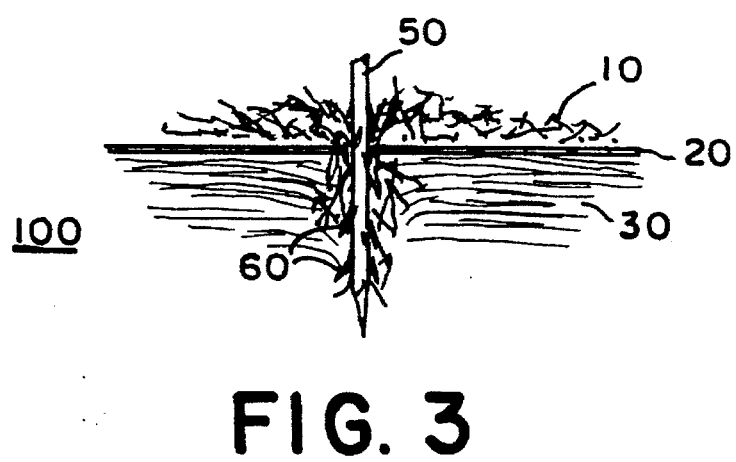
FIG. 3: is an enlarged view of an aperture of FIG. 2 illustrating how selected fibers from the fibrous top layer can be carried by the piercing barbed needle so as to introduce fibers into, the bottom layer through the generally opaque middle layer.

Referring now to FIGS. 1–3, the preferred facing material 100 and method for manufacturing this material will now be described in detail. The facing material 100 of this invention preferably includes three layers of material: a top fibrous layer 10, preferably made from a non-retentive hydrophobic web, a generally opaque apertured middle layer 20, preferably a thin, plastic film, and a bottom layer 30, preferably a hydrophilic web of fibrous material capable of pulling fluid by capillary action. The generally opaque middle layer 20 is preferably laminated between the hydrophobic and the hydrophilic webs.

Using a bed of barbed needles of a needle punch, examples of which are substantially described in FIGS. 4–6, portions of the fibrous top layer 10 desirably are pulled through the generally opaque middle layer 20 to contact and entangle with the bottom layer 30. The length, number of barbs 60 and cutting surfaces may be varied within the understanding of those of ordinary skill in the art with acceptable results. Both single blade, FIG. 4, and double blade, FIG. 6, designs can be employed, however, it is believed that short cutting blades, i.e. less than 2 inches, with less than about 4 barbs would be best suited to this invention.

The resulting structure of the facing material 100 is illustrated in FIGS. 2 and 3. The barbed needles 50 can pull the fibers of the fibrous top layer 10 in a preferred single direction so that hydrophobic fibers are present on both sides of the generally opaque middle layer 20, leaving hydrophilic fibers substantially only on one side of this middle layer 20. Since the entanglement process is done through the film of the generally opaque middle layer 20, the latter becomes apertured. The resulting composite structure preferably consists of a top hydrophobic, non-retentive layer extending through an opaque film into a hydrophilic layer which is capable of generating a greater capillary pressure. Thus, body fluid deposited on the hydrophobic side would be pulled into the hydrophilic layer and would therefore be contained and camouflaged under the opaque film. The capillary pressure gradient between the two sides of the generally opaque middle layer 20 can be established by a proper selection of fibers as substantially described below.

The fibrous top layer 10 of this invention will now be described. Suitable fibers for the fibrous top layer 10 are fibers with a hydrophobic surface having a denier of about three or greater. This corresponds to a diameter greater than about $6.6 \times 10^{-4}$ inches on a round cross section. Preferably, the fibers are polyester (polyethyleneterephthalate-PET), polypropylene, polyethylene and/or acrylic with a denier greater than about 3, and preferably about 3–15 ($6.6 \times 10^{-4}$ to about $19 \times 10^{-4}$ inches on a round cross section). The fibers can be treated with hydrophobic finishing materials such as perfluoro or silicon compounds, to establish a contact angle $\theta$ preferably greater than or equal to about 90°. Other fibers such as nylon, acetate, and spandex can be used if the above treatment is performed on them. The fibrous top layer preferably comprises more than about 50% of the overall thickness of the facing material 100, yet, preferably less than about 0.15 inches.

The generally opaque middle layer 20 is preferably an opaque film of polyethylene and/or polypropylene of a nominal thickness of about 0.2–2 mils and can comprise fillers and/or pigments to render the film more opaque. Other soft films such as PVC poly(ethylene-vinyl acetate), polyester and other polyolefins, are suitable as well.

The bottom layer 30 is preferably prepared from fine hydrophilic fibers in order to create a strong capillary action. These fibers may contain cellulosic fibers, such as wood pulp, rayon, hydrophilic nylon and/or other fine fibers of less than about 3 denier which have been treated to be hydrophilic. The surface treatment should render the fiber surface wettable, with $\theta$ being less than about 90°, and preferably equal to about 0°. This can be accomplished through the application of sufficient water soluble polymers or silica to the fibers.

In addition to the above, it is preferable that the webs of this invention include low melting fibers, so called "binder fibers" in each of the fibrous layers so that their structure does not change drastically during use. Other means to stabilize each layer, such as binder resins, etc. are also suitable. It is important to maintain an open structure with large pores in the body-facing fibrous top layer, and a smaller pore structure in the hydrophilic bottom layer beneath the generally opaque middle layer to assure effective removal of fluid away from the body. In this regard, it is preferred that the fibrous top layer of this invention comprise a density of less than about 0.1 g/cc and that the bottom layer comprise a density of greater than about 0.1 g/cc. Although needle punching techniques have been described, it is expected that those familiar with making facing materials may be able to use male-female type perf-embossing to provide a similar product. See U.S. Pat. Nos. 4,605,402 and 3,817,827, which are incorporated by reference. Such techniques, to be effective, must perforate the opaque middle layer and preferably push fibers from the top layer through these perforations.

Other methods for making the products of this invention may include the use of water jets.

The benefits of this invention are illustrated in the context of the following examples.

EXAMPLE I

A 0.7 ounce per square yard web was prepared from a 5.5 denier hollofil polyester using a carding machine. The fiber surface was washed with water to remove any previous hydrophilic treatment. A commercial crepe tissue made from cellulosic fibers and a binder for wet strength, basis weight of about 0.58 ounces per square yard, was used as a bottom wicking layer. A 1 mil thick, white pigmented polyethylene film was placed between the above web and tissue. Using the previously described barbed needle arrangement in an art recognized needle punch apparatus, holes were made in the film starting from the hydrophobic web side. Thus, some of the hydrophobic polyester fibers were pulled through the polyethylene film and entangled with the tissue paper underneath. The cover was placed on the absorbent core of a commercial sanitary napkin and one milliliter of synthetic test fluid was dropped on it. After one minute, all of the fluid was pulled and hidden under the film layer, resulting in a dry and clean surface.

EXAMPLE II

Two different fiber blends were prepared separately: a 75% 5.5 denier polyester hollofil and a 25% bicomponent thermoplastic binder fiber having a polyethylene sheath and a polyester core. The other fiber blend contained 75% 1.5 denier rayon and 25% thermoplastic binder fiber. The first blend was heated for five minutes without pressure to form a stable, low density web with a density of about 0.035 grams per cubic centimeter. The second blend was heated and pressed to form a web with a density of about 0.2 grams per cubic centimeter. An opaque polypropylene film, having a thickness of about 1 mil was placed between the two webs and the same punching operation as described in Example 1 was performed first through the low density web, then through the film and into the high density web. Again, after one minute, one milliliter of synthetic test fluid was pulled and hidden under the film layer, resulting in a dry and clean surface.

From the foregoing, it can be realized that this invention provides improved facing materials suitable for use in diapers and sanitary napkins and a method for producing these facing materials. The resulting composite structure provides a clean/dry body facing surface for absorbent products without sacrificing the comfort associated with a fibrous, textile facing. Moreover, the composite has high opacity and hides the staining of the underlying central absorbent effectively. Although various embodiments have been illustrated, this was for the purpose of describing, but not limiting the invention. Various modifications, which will become apparent to one skilled in the art, are within the scope of this invention described in the attached claims.

We claim as our invention:

1. A facing material suitable for use in diapers and sanitary napkins, comprising: a fibrous top layer for engaging a body fluid; a generally opaque apertured middle layer that substantially hides body fluids contained below the middle layer; and a bottom layer having a capillary structure for drawing said body fluid from said fibrous top layer, at least a portion of said fibrous top layer extending downward through said middle layer for communicating with said bottom layer and for providing fluid transfer from said fibrous top layer into said bottom layer.

2. The facing material of claim 1 having a thickness of less than about 0.15 inches.

3. The facing material of claim 1 wherein said fibrous top layer comprises a hydrophobic surface.

4. The facing material of claim 3 wherein said fibrous top layer comprises fibers having a denier of about 3 or greater.

5. The facing material of claim 3 wherein said fibrous top layer comprises fibers having a denier of about 3 to about 15.

6. The facing material of claim 5 wherein said fibers are treated with a hydrophobic finishing material, whereby said fibers establish a capillary contact angle of at least about 90°.

7. The facing material of claim 6 wherein said finishing material comprises a perfluro or silicon compound.

8. The facing material of claim 1 wherein said middle layer comprises a polymeric film.

9. The facing material of claim 8 wherein said opaque film comprises a thickness of about 0.0002 to 0.002 inch.

10. The facing material of claim 9 wherein said opaque film comprises polyethylene, polypropylene, or a combination thereof.

11. The facing material of claim 1 wherein said bottom layer comprises a hydrophilic surface.

12. The facing material of claim 11 wherein said bottom layer comprises a plurality of hydrophilic fibers having a denier of less than about 3.

13. The facing material of claim 11 wherein said hydrophilic fibers are treated with a hydrophilic finishing material for providing a capillary contact angle of less than about 90°.

14. A facing material suitable for use in diapers and sanitary napkins, comprising:
    a fibrous top layer for engaging body fluid, said fibrous top layer comprising a plurality of hydrophobic fibers having a denier of about 3 or greater;
    a generally opaque polymeric middle layer which substantially hides body fluids contained below the middle layer having a thickness of from about 0.0002 to 0.002 inch; and a bottom layer capable of generating a greater capillary pressure than said fibrous top layer, said polymeric middle layer comprising apertures therethrough whereby a portion of said fibers of said fibrous top layer are disposed through said apertures and into said bottom layer for providing fluid transfer from said fibrous top layer into said bottom layer.

15. The facing material of claim 14 wherein said fibrous top layer comprises a density of less than about 0.1 g/cc.

16. The facing material of claim 14 wherein said bottom layer comprises a density of greater than about 0.1 g/cc.

17. The facing material of claim 14 wherein said middle layer comprises a thickness of about 0.001 inch.

18. The facing material of claim 14 having a thickness of about 0.15 inches or less.

19. The facing material of claim 14 wherein said facing material has a thickness, and wherein said fibrous top layer comprises greater than about half said thickness of said facing material.

20. A method of preparing a facing material suitable for use in diapers and sanitary napkins, comprising:
    (a) providing a tri-layered flexible composite including a fibrous top layer comprising a hydrophobic surface for engaging body fluid, a middle layer and a bottom layer having a capillary structure for drawing body fluid, said middle layer having sufficient opacity to prevent observation of menstrual fluid contained within said bottom layer; and
    (b) perforating said composite to provide a plurality of apertures through said middle layer and to dispose a portion of said fibrous top layer downward through said apertures for communicating with said bottom layer and for providing fluid transfer from said fibrous top layer into said bottom layer.

21. The method of claim 20 wherein said perforating step (b) comprises needle punching said tri-layered flexible composite.

22. A facing material suitable for use in diapers and sanitary napkins, comprising:
    a top layer comprising a plurality of hydrophobic fibers for engaging a body fluid;
    a generally opaque apertured layer that substantially hides body fluids contained below the apertured layer, at least a portion of the fibers of said top layer extending downward through said apertured layer for providing for fluid transfer from said top layer through said apertured layer.

23. The facing material of claim 22 wherein said apertured layer comprises a polymeric film having a thickness of from about 0.0002 to 0.002 inch.

* * * * *